(12) United States Patent
Bur et al.

(10) Patent No.: US 7,981,886 B2
(45) Date of Patent: Jul. 19, 2011

(54) ANTIBIOTICS DERIVATIVES

(75) Inventors: Daniel Bur, Therwil (CH); Christian Hubschwerlen, Durmenach (FR); Jean-Philippe Surivet, Kembs (FR); Cornelia Zumbrunn-Acklin, Basel (CH)

(73) Assignee: Actelion Pharmaceutical Ltd., Allschwil (CH)

( * ) Notice: Subject to any disclaimer, the term of this patent is extended or adjusted under 35 U.S.C. 154(b) by 639 days.

(21) Appl. No.: 11/915,179

(22) PCT Filed: May 24, 2006

(86) PCT No.: PCT/IB2006/051661
§ 371 (c)(1),
(2), (4) Date: Jul. 3, 2008

(87) PCT Pub. No.: WO2006/126171
PCT Pub. Date: Nov. 30, 2006

(65) Prior Publication Data
US 2008/0280888 A1    Nov. 13, 2008

(30) Foreign Application Priority Data

May 25, 2005    (EP) .................. PCT/EP2005/005643

(51) Int. Cl.
| C07D 417/12 | (2006.01) |
| C07D 413/12 | (2006.01) |
| C07D 409/12 | (2006.01) |
| A61K 31/5415 | (2006.01) |
| A61K 31/538 | (2006.01) |

(52) U.S. Cl. ........... 514/228.2; 544/48; 544/51; 544/52; 514/228.5

(58) Field of Classification Search ................ 514/228.2; 514/228.5; 544/48, 51, 52
See application file for complete search history.

(56) References Cited

FOREIGN PATENT DOCUMENTS
EP    A1-0863139    9/1998
WO    WO92/06086 A    9/1991

OTHER PUBLICATIONS

Vippagunta et al, "Crystalline Solids" Advanced Drug Delivery Reviews, vol. 48, pp. 3-26 (2001).*
Gavezzotti, "Are Crystal Structures Predictable?" Accounts of Chemical Research, vol. 27, pp. 309-314 (1994).*
Wolff Manfred E. "Burger's Medicinal Chemistry, 5ed, Part 1" John Wiley & Sons, 1995, pp. 975-977.*
Banker, G.S. et al, "Modern Pharmaceutics, 3ed." Marcel Dekker, New York, 1996, pp. 451 and 596.*
PCT/IB2006/051661—PCT Notification Concerning Submission or Transmittal of Priority Document.
PCT/IB2006/051661—PCT Request.
PCT/IB2006/051661—PCT Written Opinion.

* cited by examiner

Primary Examiner — Kahsay T Habte
(74) Attorney, Agent, or Firm — Hunton & Williams LLP

(57) ABSTRACT

The invention relates to antibiotic derivatives of formula I

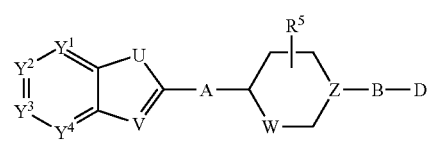

wherein:
A represents —O—, S, —C(═O)—, —C(═NOR$^6$)—;
Z—B represents NCH$_2$CH$_2$, NCOCH$_2$, NCH$_2$CO, NCH$_2$CH(OH), CHN(R$^8$)CH$_2$ or CHN(R$^8$)CO;
D represents binuclear heteroaryl;
Y$^1$ represents —CR$^1$— or —N—, Y$^2$ represents —CR$^2$— or —N—, Y$^3$ represents —CR$^3$— or —N— and Y$^4$ represents —CR$^4$— or —N—;
U represents —NH—, —O— or —S— and V represents —N— or —CH—;
W represents —CH$_2$—, —O— or —NR$^7$—;
R$^1$ represents H, methyl, ethyl or halogen;
R$^2$, R$^3$ and R$^4$ each represent independently H, C$_1$-C$_4$ alkyl, halogen, or C$_1$-C$_4$ alkoxy;
R$^5$ represents H, C$_1$-C$_4$ alkyl or fluorine;
R$^6$ represents H, C$_1$-C$_4$ alkyl or aryl-C$_1$-C$_4$ alkyl;
R$^7$ represents H, C$_1$-C$_4$ alkyl, aryl-C$_1$-C$_4$ alkyl or —CH$_2$—COOH;
R$^8$ represents H, C$_1$-C$_4$ alkyl or —CH$_2$—COOH;
with the provisos that
  if Z—B represents NCH$_2$CH$_2$, NCOCH$_2$, NCH$_2$CO or NCH$_2$CH(OH), then W represents —CH$_2$—;
  if A represents O or S, then W represents —CH$_2$—; and
  only one or two of Y$^1$, Y$^2$, Y$^3$ and Y$^4$ can represent N at the same time.

18 Claims, No Drawings

ANTIBIOTICS DERIVATIVES

CONTINUITY DATA

This application is a national stage entry of PCT/IB2006/051661, filed on May 24, 2006, which in turn claims priority to PCT/EP2005/005643, filed on May 25, 2005; both of which applications are hereby incorporated by reference in their entirety.

FIELD OF INVENTION

The present invention concerns novel antibiotics, pharmaceutical antibacterial composition containing them and use thereof in the manufacture of a medicament for the treatment of infections (e.g. bacterial infection). These compounds are useful antimicrobial agents effective against a variety of human and veterinary pathogens including among others Gram positive and Gram negative aerobic and anaerobic bacteria and mycobacteria.

BACKGROUND OF INVENTION

The intensive use of antibiotics has exerted a selective evolutionary pressure on micro-organisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:

- *S. aureus* is resistant to β-lactam, quinolone and now even to vancomycin;
- *S. pneumoniae* is becoming resistant to penicillin, quinolone and new macrolides;
- Enterococci are quinolone and vancomycin resistant and β-lactams are inefficacious against these strains;
- Enterobacteriacea are cephalosporin and quinolone resistant;
- *P. aeruginosa* are β-lactam and quinolone resistant.

Further new emerging organisms like *Acinetobacter* which have been selected during therapy with the currently used antibiotics are becoming a real problem in hospital settings.

In addition, microorganisms that are causing persistent infections are increasingly being recognized as causative agents or cofactors of severe chronic diseases like peptic ulcers or heart diseases.

DETAILED DESCRIPTION OF THE INVENTION

This invention provides compounds of formula I

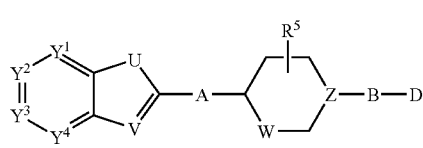

wherein:
A represents —O—, S, —C(=O)—, —C(=NOR$^6$)—;
Z—B represents NCH$_2$CH$_2$, NCOCH$_2$, NCH$_2$CO, NCH$_2$CH(OH), CHN(R$^8$)CH$_2$ or CHN(R$^8$)CO;
D represents binuclear heteroaryl;
U represents —NH—, —O— or —S—;
V represents —N— or —CH—;
W represents —CH$_2$—, —O— or —NR$^7$—;
Y$^1$ represents —CR$^1$— or —N—;
Y$^2$ represents —CR$^2$— or —N—;
Y$^3$ represents —CR$^3$— or —N—;
Y$^4$ represents —CR$^4$— or —N—;
R$^1$ represents H, methyl, ethyl or halogen;
R$^2$, R$^3$ and R$^4$ each represent independently H, C$_1$-C$_4$ alkyl, halogen, or C$_1$-C$_4$ alkoxy;
R$^5$ represents H, C$_1$-C$_4$ alkyl or fluorine;
R$^6$ represents H, C$_1$-C$_4$ alkyl or aryl-C$_1$-C$_4$ alkyl;
R$^7$ represents H, C$_1$-C$_4$ alkyl, aryl-C$_1$-C$_4$ alkyl or —CH$_2$—COOH;
R$^8$ represents H, C$_1$-C$_4$ alkyl or —CH$_2$—COOH;
with the provisos that
  if Z—B represents NCH$_2$CH$_2$, NCOCH$_2$, NCH$_2$CO or NCH$_2$CH(OH), then W represents —CH$_2$—;
  if A represents O or S, then W represents —CH$_2$—; and
  only one or two of Y$^1$, Y$^2$, Y$^3$ and Y$^4$ can represent N at the same time.

The compounds of formula I have antibacterial activity and are suitable for use as chemotherapeutic active compounds in human and veterinary medicine.

A further embodiment of the bicyclic derivatives of the above formula I relates to their prodrugs, their tautomers, their optically pure enantiomers, mixtures of enantiomers, racemates, optically pure diastereoisomers, mixtures of diastereoisomers, diastereoisomeric racemates, mixture of diastereoisomeric racemates, meso forms, pharmaceutically acceptable salts, solvent complexes and morphological forms thereof. Particularly preferred are the optically pure enantiomers, optically pure diastereoisomers, meso forms, pharmaceutically acceptable salts, solvent complexes and morphological forms.

Any reference to a compound of formula I is thus to be understood as referring also to configurational isomers, mixtures of enantiomers such as racemates, diastereomers, mixtures of diastereomers, diastereomeric racemates, and mixtures of diastereomeric racemates, as well as salts, solvent complexes, and morphological forms of such compounds, as appropriate and expedient.

The present invention also relates to pro-drugs of a compound of formula I that convert in vivo into the compound of formula I as such. Any reference to a compound of formula I is therefore to be understood as referring also to the corresponding pro-drugs of the compound of formula I, as appropriate and expedient.

The following paragraphs provide definitions of the various chemical moieties for the compounds according to the invention and are intended to apply uniformly throughout the specification and claims unless an otherwise expressly set out definition provides a broader or narrower definition.

The term "C$_1$-C$_4$ alkyl" refers to a saturated straight or branched chain alkyl group, containing one to four carbon atoms, for example methyl, ethyl, n-propyl, iso-propyl, n-butyl, iso-butyl, sec-butyl and tert-butyl. Similarly, the term "C$_1$-C$_3$ alkyl" refers to a saturated straight or branched chain alkyl group, containing one to three carbon atoms (e.g. methyl, ethyl or iso-propyl).

The term "C$_1$-C$_4$ alkoxy" refers to a saturated straight or branched chain alkoxy group, containing one to four carbon atoms, for example methoxy, ethoxy, n-propoxy, iso-propoxy, n-butoxy, iso-butoxy, sec-butoxy and tert-butoxy. Similarly, the term "C$_1$-C$_3$ alkoxy" refers to a saturated straight or branched chain alkoxy group, containing one to three carbon atoms (e.g. methoxy, ethoxy or iso-propoxy).

The term "halogen" refers to fluorine, chlorine, bromine or iodine, preferably to fluorine or chlorine.

The term "binuclear heteroaryl" refers to an aromatic 5- or 6-membered ring where one, two or more ring-carbon atoms may be replaced by an oxygen, nitrogen or sulphur atom, which ring is annealed to an aromatic or non-aromatic 5- or 6-membered ring where in turn one, two or more ring-carbon atoms may be replaced by an oxygen, nitrogen or sulphur atom, provided that the resulting binuclear heteroaryl group contains at least one heteroatom. Examples of the first mentioned aromatic ring capable of forming said "binuclear heteroaryl" are: phenyl, thiophenyl, furyl, pyridyl, imidazolyl, pyrazolyl, pyrrolyl, oxazolyl, isoxazolyl, thiazolyl, 1,2,3-triazolyl, 1,2,4-triazolyl, pyrazinyl, pyrimidinyl and pyridazinyl. Examples of the resulting "binuclear heteroaryl" are: benzofuranyl, benzimidazolyl, benzothiazolyl, benzo[1,3]dioxol-5-yl, 2,3-dihydro-benzo[1,4]dioxin-6-yl, 4H-benzo[1,4]oxazin-3-one-6-yl, 4H-benzo[1,4]thiazin-3-one-6-yl, 3-oxo-3,4-dihydro-2H-benzo[1,4]thiazin-6-yl, 1H-pyrido[2,3-b][1,4]thiazin-2-one-7-yl, 2,3-dihydro-[1,4]dioxino[2,3-c]pyridin-7-yl, 2,3-dihydro-[1,4]dioxino[2,3-b]pyridin-7-yl, 4H-pyrido[3,2-b][1,4]oxazin-3-one-6-yl, 3,4-dihydro-2H-pyrido[3,2-b]thiazin-6-yl, 3-oxo-3,4-dihydro-2H-pyrido[3,2-b]thiazin-6-yl, 3,4-dihydro-1H-quinolin-2-one-7-yl, 3,4-dihydro-1H-quinoxalin-2-one-7-yl, 2-oxo-3,4-dihydro-1H-[1,8]naphthyridin-6-yl, 6,7-dihydro-[1,4]dioxino[2,3-d]pyrimidin-2-yl, 2-oxo-2,3-dihydro-1H-pyrido[3,4-b][1,4]oxazin-7-yl, 2-oxo-2,3-dihydro-1H-pyrido[2,3-b][1,4]oxazin-7-yl, benzo[1,2,5]thiadiazol-5-yl, benzofuran-3-yl and 7-fluoro-4H-benzo[1,4]thiazin-3-one-6-yl. Any heteroaryl group as defined herein may be substituted with one, two or more substituents independently selected from halogen, $C_1$-$C_4$ alkyl, trifluoromethyl, $C_1$-$C_4$ alkoxy and trifluoromethoxy. In addition, the non-aromatic ring of a binuclear heteroaryl may be substituted once by oxo.

The term "aryl" refers to an aromatic cyclic group with one, two or three rings, having five to 14 carbon ring-atoms preferably from five or six to ten carbon ring-atoms, for example phenyl or naphthyl groups. Any aryl group as defined herein may be substituted with one, two or more substituents independently selected from halogen, $C_1$-$C_4$ alkyl, trifluoromethyl, $C_1$-$C_4$ alkoxy and trifluoromethoxy. Specific examples of aryl are phenyl, 2-fluorophenyl, 3-fluorophenyl, 4-fluorophenyl, 4-methoxyphenyl, 4-methylphenyl, 2-trifluoromethylphenyl, 3-trifluoromethylphenyl 4-trifluoromethylphenyl, 4-trifluoromethoxy-phenyl, 2,4-difluorophenyl, 3,4-difluorophenyl, 2,4-dimethoxyphenyl and 2,4-dimethylphenyl.

The aforegoing groups "$C_1$-$C_4$ alkyl" and "aryl" when combined to form the group aryl-$C_1$-$C_4$ alkyl have the same exemplary meaning as their constituents discussed above. As brief examples only, the combination aryl-$C_1$-$C_4$ alkyl can mean benzyl, phenethyl, naphthylmethyl, 4-fluorobenzyl, 2,4-dimethoxybenzyl or 2,4-di-trifluoromethyl-phenethyl.

Preferred compounds of formula I are the compounds of formula $I_{CE}$

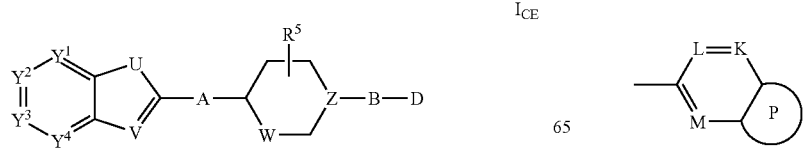

$I_{CE}$ wherein:
A represents —O—, —C(=O)—, C=NOR$^6$;
Z—B represents NCH$_2$CH$_2$, NCH$_2$CO, NCH$_2$CH(OH) or CHN(R$^8$)CH$_2$;
D is selected from the group consisting of

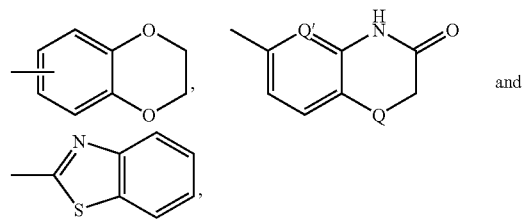

Q being —O— or —S— and Q' being —CH— or —N—;
U represents —NH—, —O— or —S—;
V represents —N— or —CH—;
W represents —CH$_2$— or —O—;
Y$^1$ represents —CR$^1$— or —N—;
Y$^2$ represents —CR$^2$—;
Y$^3$ represents —CR$^3$—;
Y$^4$ represents —CR$^4$—;
R$^1$ represents H, methyl or ethyl;
R$^2$ represents H or $C_1$-$C_4$ alkoxy;
R$^3$ represents H or $C_1$-$C_4$ alkoxy;
R$^4$ represents H, $C_1$-$C_4$ alkyl or $C_1$-$C_4$ alkoxy;
R$^5$ represents H;
R$^6$ represents H;
R$^8$ represents H;
with the provisos that
  if Z—B represents NCH$_2$CH$_2$, NCH$_2$CO or NCH$_2$CH(OH), then W represents CH$_2$; and
  if A represents —O—, then W represents —CH$_2$—.

Preferred compounds of formula I are those wherein at least one of the following characteristics is present:
A representing —C(=O)—;
Z—B representing CH—NH—CH$_2$;
U representing —S—;
W representing —CH$_2$— or —O—, and in particular —CH$_2$—;
Y$^4$ being —CR$^4$—, one of Y$^1$, Y$^2$ and Y$^3$ being —N— while the remaining are —CR$^1$—, —CR$^2$— or —CR$^3$— respectively, or, alternatively, Y$^1$, Y$^2$, Y$^3$ and Y$^4$ being —CR$^1$—, —CR$^2$—, —CR$^3$— and —CR$^4$— respectively;
R$^1$ being H;
R$^2$ and R$^3$ being both H;
R$^4$ being $C_1$-$C_3$ alkyl or $C_1$-$C_3$ alkoxy;
R$^5$ being H;
R$^8$ being H.

Another category of quite preferred compounds of formula I consists of those wherein W represents —O—.

Preferred embodiments of D are "binuclear heteroaryl" groups of the formula:

wherein P is a ring selected from

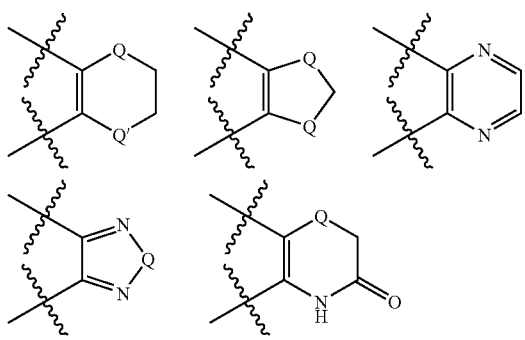

wherein
Q is —O— or —S— and Q' is —O— or —S—;
K, L and M are each independently —N— or —CR$^9$—; and R$^9$ is hydrogen or fluorine.

Still preferred embodiments of D are 2,3-dihydro-benzo[1,4]dioxin-6-yl, benzo[1,3]dioxol-5-yl, 4H-benzo[1,4]oxazin-3-one-6-yl, 4H-benzo[1,4]thiazin-3-one-6-yl, 7-fluoro-4H-benzo[1,4]thiazin-3-one-6-yl, 2,3-dihydro[1,4]dioxino[2,3-c]pyridin-7-yl, 2,3-dihydro[1,4]dioxino[2,3-b]pyridin-6-yl, 4H-pyrido[3,2-b][1,4]thiazin-3-one-6-yl, 2-oxo-1H-pyrido[2,3-b][1,4]thiazin-7-yl, benzo[1,2,5]thiadiazol-5-yl and benzothiazol-2-yl.

Even preferred embodiments of D are "binuclear heteroaryl" groups of the formula:

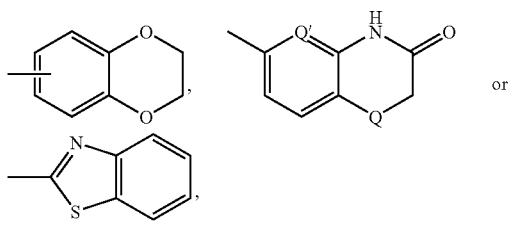

wherein Q is —O— or —S— and Q' is —CH— or —N—.

Besides, compounds wherein W is —CH$_2$—, R$^5$ is H, Z—B represents CHN(R$^8$)CH$_2$ or CHN(R$^8$)CO and the two substituents A and B are trans configured are preferred.

Further preferred are compounds of formula I wherein W is —O— and the group

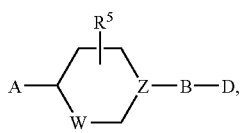

has the following partial structure:

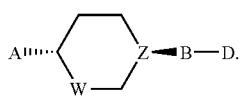

Most preferred compounds are:
6-{[4-(benzothiazole-2-carbonyl)-cyclohexylamino]-methyl}-4H-benzo[1,4]thiazin-3-one;
6-{[trans-4-(benzothiazole-2-carbonyl)-cyclohexylamino]-methyl}-4H-benzo[1,4]oxazin-3-one;
benzothiazol-2-yl-{trans-4-[(2,3-dihydro-benzo[1,4]dioxin-6-ylmethyl)-amino]-cyclohexyl}-methanone;
6-{[trans-4-(4-methyl-benzothiazole-2-carbonyl)-cyclohexylamino]-methyl}-4H-benzo[1,4]thiazin-3-one;
{trans-4-[(2,3-dihydro-benzo[1,4]dioxin-6-ylmethyl)-amino]-cyclohexyl}-(4-methyl-benzothiazol-2-yl)-methanone;
{trans-4-[(2,3-dihydro-benzo[1,4]dioxin-6-ylmethyl)-amino]-cyclohexyl}-(5-methoxy-benzothiazol-2-yl)-methanone;
6-{[trans-4-(6-methoxy-benzothiazole-2-carbonyl)-cyclohexylamino]-methyl}-4H-benzo[1,4]thiazin-3-one;
6-{[trans-4-(6-methoxy-benzothiazole-2-carbonyl)-cyclohexylamino]-methyl}-4H-benzo[1,4]oxazin-3-one;
{trans-4-[(2,3-dihydro-benzo[1,4]dioxin-6-ylmethyl)-amino]-cyclohexyl}-(6-methoxy-benzothiazol-2-yl)-methanone;
6-{[trans-4-(4-methoxy-benzothiazole-2-carbonyl)-cyclohexylamino]-methyl}-4H-benzo[1,4]thiazin-3-one;
6-{[trans-4-(4-methoxy-benzothiazole-2-carbonyl)-cyclohexylamino]-methyl}-4H-benzo[1,4]oxazin-3-one;
{trans-4-[(2,3-dihydro-benzo[1,4]dioxin-6-ylmethyl)-amino]-cyclohexyl}-(4-methoxy-benzothiazol-2-yl)-methanone;
{trans-4-[(benzothiazol-2-ylmethyl)-amino]-cyclohexyl}-(4-methoxy-benzothiazol-2-yl)-methanone;
6-{[trans-4-(4-ethoxy-benzothiazole-2-carbonyl)-cyclohexylamino]-methyl}-4H-benzo[1,4]thiazin-3-one;
6-{[trans-4-(4-ethoxy-benzothiazole-2-carbonyl)-cyclohexylamino]-methyl}-4H-benzo[1,4]oxazin-3-one;
{trans-4-[(2,3-dihydro-benzo[1,4]dioxin-6-ylmethyl)-amino]-cyclohexyl}-(4-ethoxy-benzothiazol-2-yl)-methanone;
6-{[trans-4-(4-methoxy-7-methyl-benzothiazole-2-carbonyl)-cyclohexylamino]-methyl}-4H-benzo[1,4]thiazin-3-one;
{trans-4-[(2,3-dihydro-benzo[1,4]dioxin-6-ylmethyl)-amino]-cyclohexyl}-(4-methoxy-7-methyl-benzothiazol-2-yl)-methanone;
6-{[trans-4-(benzo[b]thiophene-2-carbonyl)-cyclohexylamino]-methyl}-4H-benzo[1,4]thiazin-3-one;
6-{[trans-4-(benzo[b]thiophene-2-carbonyl)-cyclohexylamino]-methyl}-4H-benzo[1,4]oxazin-3-one;
benzo[b]thiophen-2-yl-{trans-4-[(2,3-dihydro-benzo[1,4]dioxin-6-ylmethyl)-amino]-cyclohexyl}-methanone;
6-{[trans-4-(thiazolo[5,4-b]pyridine-2-carbonyl)-cyclohexylamino]-methyl}-4H-benzo[1,4]thiazin-3-one;
6-{[trans-4-(4-methoxy-benzothiazole-2-carbonyl)-cyclohexylamino]-methyl}-4H-pyrido[3,2-b][1,4]thiazin-3-one;
6-({trans-4-[(4-methoxy-benzothiazol-2-yl)-methoxyimino-methyl]-cyclohexylamino}-methyl)-4H-pyrido[3,2-b][1,4]thiazin-3-one;
6-{[trans-4-(4-methoxy-benzooxazole-2-carbonyl)-cyclohexylamino]-methyl}-4H-benzo[1,4]oxazin-3-one;
(2,3-dihydro-benzo[1,4]dioxin-6-ylmethyl)-[trans-4-(4-methoxy-benzothiazol-2-yloxy)-cyclohexyl]-amine;
6-{[trans-4-(4-methoxy-benzothiazol-2-yloxy)-cyclohexylamino]-methyl}-4H-benzo[1,4]oxazin-3-one;
6-{[trans-4-(4-methoxy-benzothiazol-2-yloxy)-cyclohexylamino]-methyl}-4H-benzo[1,4]thiazin-3-one;
(3R,6S)-6-{[6-(4-methoxy-benzothiazole-2-carbonyl)-tetrahydro-pyran-3-ylamino]-methyl}-4H-pyrido[3,2-b][1,4]thiazin-3-one;

(3R,6S)-6-{[6-(4-methoxy-benzothiazole-2-carbonyl)-tetrahydro-pyran-3-ylamino]-methyl}-4H-benzo[1,4]thiazin-3-one;
(3R,6S)-6-({6-[hydroxyimino-(4-methoxy-benzothiazol-2-yl)-methyl]-tetrahydro-pyran-3-ylamino}-methyl)-4H-pyrido[3,2-b][1,4]thiazin-3-one;
{1-[2-(2,3-dihydro-benzo[1,4]dioxin-6-yl)-ethyl]-piperidin-4-yl}-(4-methoxy-benzothiazol-2-yl)-methanone;
1-(2,3-dihydro-benzo[1,4]dioxin-6-yl)-2-[4-(4-methoxy-benzothiazole-2-carbonyl)-piperidin-1-yl]-ethanone;
6-{2-[4-(4-methoxy-benzothiazole-2-carbonyl)-piperidin-1-yl]-acetyl}-4H-benzo[1,4]oxazin-3-one;
6-{2-[4-(4-methoxy-benzothiazole-2-carbonyl)-piperidin-1-yl]-acetyl}-4H-benzo[1,4]thiazin-3-one;
{1-[2-(2,3-dihydro-benzo[1,4]dioxin-6-yl)-2-hydroxy-ethyl]-piperidin-4-yl}-(4-methoxy-benzothiazol-2-yl)-methanone;
and pharmaceutically acceptable salts thereof.

A further aspect of the invention relates to the compounds of formula I (or $I_{CE}$), or their pharmaceutically acceptable salts, as medicaments.

The compounds according to the invention are particularly active against bacteria and bacteria-like organisms. They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus,* or *Peptostreptococcus* spp.; pharyngitis, rheumatic fever, and glomerulonephritis related to infection by *Streptococcus pyogenes*, Groups C and G streptococci, *Corynebacterium diphtheriae*, or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans,* including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus,* etc.), *Streptococcus pyogenes, Streptococcus agalactiae*, Streptococcal groups C-F (minute colony streptococci), viridans streptococci, *Corynebacterium minutissimum, Closfridium* spp., or *Bartonella henselae*; uncomplicated acute urinary tract infections related to infection by *Staphylococcus aureus*, coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrhoeae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae*.

Compounds of formula I (or $I_{CE}$) according to the present invention are further useful for the preparation of a medicament for the treatment of infections that are mediated by bacteria such as *E. coli, Klebsiella pneumoniae* and other enterobacteriaceae, *Acinetobacter* spp., *Stenothrophomonas maltophilia, Neisseria meningitidis, Bacillus cereus, Bacillus anthracis, Corynebacterium* spp., *Propionibacterium acnes* and bacteroide spp.

Compounds of formula I (or $I_{CE}$) according to the present invention are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

As well as in humans, bacterial infections can also be treated in other species like pigs, ruminants, horses, dogs, cats and poultry.

The present invention also relates to pharmaceutically acceptable salts, or solvates and hydrates, respectively, and to compositions and formulations of compounds of formula I.

The expression "pharmaceutically acceptable salts" encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanedisulfonic acid, p-toluenesulfonic acid, salicylic acid, succinic acid, trifluoroacetic acid, and the like that are non toxic to living organisms or, in case the compound of formula I is acidic in nature, with an inorganic base like an alkali or earth alkali base, e.g. sodium hydroxide, potassium hydroxide, calcium hydroxide and the like. For other examples of pharmaceutically acceptable salts, reference can be made notably to "Salt selection for basic drugs", *Int. J. Pharm.* (1986), 33, 201-217.

Compounds of formula I (or $I_{CE}$) may be solvated, especially hydrated. The hydration can occur during the process of production or as a consequence of the hygroscopic nature of the initially water free compounds of formula I (or $I_{CE}$).

A pharmaceutical composition according to the present invention contains at least one compound of formula I (or $I_{CE}$) as the active agent and optionally carriers and/or diluents and/or adjuvants, and may also contain additional known antibiotics.

As mentioned above, therapeutically useful agents that contain compounds of formula I (or $I_{CE}$), their solvates, salts or formulations are also comprised in the scope of the present invention. In general, compounds of formula I (or $I_{CE}$) can be administered, for example, perorally, e.g. as tablets, coated tablets, dragees, soft and hard gelatine capsules, pills, aqueous or oily solutions, emulsions, suspensions or syrups, rectally, e.g. in the form of suppositories, parenterally e.g. in the form of injection or infusion solutions, or topically, e.g. in the form of ointments, creams or oils.

Another aspect of the invention concerns a method for the treatment of an infectious disease comprising the administration to the patient in need thereof of a therapeutically effective amount of a compound of formula I (or $I_{CE}$).

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy,* 20th Edition, Philadelphia College of Pharmacy and Science) by bringing the described compounds of formula I and their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Besides, the compounds of formula I (or $I_{CE}$) may also be used for cleaning purposes, e.g. to remove pathogenic microbes and bacteria from surgical instruments or to make a room or an area aseptic. For such purposes, the compounds of formula I (or $I_{CE}$) could be contained in a solution or in a spray formulation.

The present invention also relates to pro-drugs that are composed of a compound of formula I (or $I_{CE}$) having a free carboxylic acid and at least one pharmacologically acceptable protective group that will be cleaved off under physiological conditions. Such prodrugs have been reviewed by Beaumont, Kevin; Webster, Robert; Gardner, Iain; Dack, Kevin in *Current Drug Metabolism* (2003), 4(6), 461-485. Examples of such promoieties are alkoxy-, aralkyloxy-, OCH($R^a$)OCOR$^b$ (e.g. pivaloyloxymethyloxy, axetil, acoxil or pentexil), OCH($R^a$)OCOOR$^b$ (e.g. proxetil, hexetil), OCH($R^a$)OR$^b$, 2-alkyloxycarbonyl-2-alkylidene-ethoxy group (e.g. bopentil), 5-alkyl[1,3]dioxol-2-one-4-yl-methyloxy (e.g. daloxate), dimethylaminoethoxy, wherein $R^a$ and $R^b$ are hydrogen, $C_1$-$C_6$ alkyl, $C_2$-$C_6$ alkenyl, $C_2$-$C_6$ alkynyl, $C_3$-$C_6$ cycloalkyl, benzyl, phenyl optionally substituted by $C_1$-$C_4$ alkyl or pyridyl. Further, if a free hydroxyl group is present on a compound of formula I, it can be protected as a prodrug of the type sulfate ($OSO_3H$), phosphate ($OPO_3H_2$), oxymethylene phosphate ($OCH_2OPO_3H_2$), succinate ($OCOCH_2CH_2COOH$), or ester of naturally occurring amino acids or a derivative thereof (e.g. dimethylaminoglycine).

A further object of this invention is a pharmaceutical composition containing, as active principle, a compound of formula I (or $I_{CE}$) or a pharmaceutically acceptable salt thereof, and at least one therapeutically inert excipient.

The invention also relates to the use of a compound of formula I (or $I_{CE}$), or of a pharmaceutically acceptable salt thereof, for the manufacture of a medicament intended to prevent or treat infections, and in particular to prevent or treat local and systemic infections caused by bacteria and bacteria-like organisms as well as disorders related to bacterial infections.

The preferences indicated for the compounds of formula I of course apply mutatis mutandis to the compounds of formula $I_{CE}$, as well as to the optically pure enantiomers, mixtures of enantiomers, racemates, optically pure diastereoisomers, mixtures of diastereoisomers, diastereoisomeric racemates, mixture of diastereoisomeric racemates, meso forms, geometric isomers, solvates, morphological forms and pharmaceutically acceptable salts of the compounds of formula I or of formula $I_{CE}$. The same applies to these compounds as medicaments, to pharmaceutical compositions containing these compounds as active principles or to the uses of these compounds for the manufacture of a medicament for the treatment of diseases according to this invention.

According to the invention, the compounds of formula I can be prepared by the process described below.

Preparation of the Compounds of Formula I

The compounds of this invention can be manufactured in accordance with the present invention by a) when manufacture of a compound of formula I wherein A represents —C(=O)— is sought, reacting a compound of the general formula II

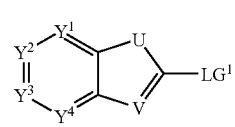

II wherein $LG^1$ represents an alkali metal (such as Li, Na or K) or MgX group, X being halogen (such as chlorine) and U, V, $Y^1$, $Y^2$, $Y^3$ and $Y^4$ are defined as above, with a compound of the formula III

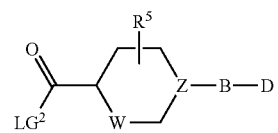

III wherein $LG^2$ is hydrogen or N($C_1$-$C_3$ alkoxy)($C_1$-$C_3$ alkyl) and Z—B, D, W and $R^5$ are defined as above, or b) reacting a compound of the formula IV

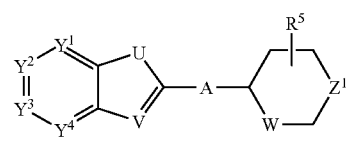

IV wherein $Z^1$ represents CH—N($R^8$)H or NH, and A, $R^5$, $R^8$, U, V, W, $Y^1$, $Y^2$, $Y^3$ and $Y^4$ are defined as above, with a compound of the general formula V

D-L$^3$   V wherein D is as above and:
when $Z^1$ in formula IV is CH—N($R^8$)H, $L^3$ is COOH, CHO or $CH_2X$ and X is halogen, methanesulfonyloxy, tosyloxy or trifluoromethylsulfonyloxy
when $Z^1$ in formula IV is NH, $L^3$ is $CH_2CH_2X$, $COCH_2X$, $CH_2COOH$ or oxiranyl and X is halogen, methanesulfonyloxy, tosyloxy or trifluoromethylsulfonyloxy or c) when manufacture of a compound of formula I wherein A represents —O— or —S— and W is —CH$_2$— is sought, reacting a compound of formula VI

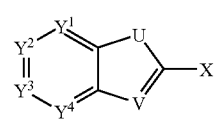

VI wherein X is an halogen and U, V, $Y^1$, $Y^2$, $Y^3$ and $Y^4$ are defined as above, with a compound of formula VII

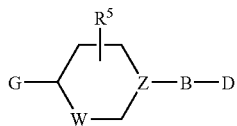

VII wherein G is an —O-alkali metal or —S-alkali metal group (such as —O—Li, —O—Na or —S—Na), W is —CH$_2$— and Z—B, D and R$^5$ are defined as above, or d) when manufacture of a compound of formula I wherein A represents —C(=O)— is sought, oxidizing a compound of formula VIII

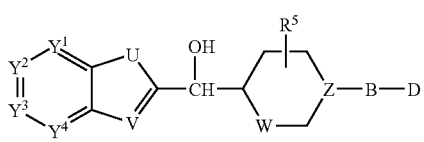

VIII wherein Z—B, D, U, V, W, Y$^1$, Y$^2$, Y$^3$, Y$^4$ and R$^5$ are as before, and when Z—B is the group CHNHCH$_2$, the NH function thereof is protected by a group selected from benzyloxycarbonyl, tert-butoxycarbonyl and allyloxycarbonyl, followed by deprotection of such benzyloxycarbonyl, tert-butoxycarbonyl and allyloxycarbonyl group, or e) when manufacture of a compound of formula I wherein A represents —C(=NOR$^6$)— is sought, reacting a compound of formula I wherein A is —C(=O)— with a hydroxylamine of formula IX

R$^6$ONH$_2$     IX wherein R$^6$ is as before, or f) when manufacture of a compound of formula I, where A represents —C(=NOR$^6$)— and R$^6$ is C$_1$-C$_4$ alkyl or aryl-C$_1$-C$_4$ alkyl is sought, reacting a compound of formula I wherein A is —C(=NOH)— with a halide of formula X

R$^6$X     X wherein X is halogen and R$^6$ is defined as above, or g) converting a compound of formula I into a prodrug or a pharmaceutically acceptable salt thereof.

The required substituted benzothiazoles, benzimidazoles, benzothiophenes, and benzofuranes of formulae II (LG$^1$=H) and VI are obtained according to known literature procedures (see e.g. the references in the examples). For example, benzothiazole derivatives can be prepared (Scheme 1) from 2-aminobenzothiazoles by reductive deamination as described in *Bioorg. Med. Chem.* (2003), 4769. 2-halobenzothiazoles are prepared by one-pot Sandmeier reaction (*J. Org. Chem.* (1977), 42, 2426). The starting 2-aminobenzothiazoles are obtained from anilines (see e.g. *J. Org. Chem.* (1980), 45, 2243; see also references in the examples).

Scheme 1

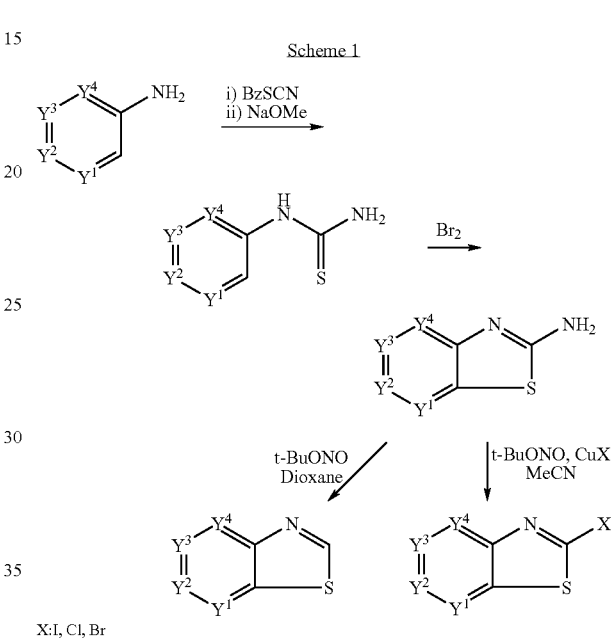

X: I, Cl, Br

Thiazolopyridines of formula II (wherein Y$^1$=N) are prepared according to literature (*Synthesis* (1974), 120).

The reactions to obtain compounds of formula I wherein A is CO or CHOH starting from compounds II and III) are preferably carried out by treating compounds of formula II wherein LG$^1$ is H between −100 and +20° C. preferably between −78 and −20° C. with either a metal alkyl such as n-BuLi, lithium diisopropylamide (LDA) or an alkylmagnesium halide such as isopropyl magnesium chloride and subsequently reacting the intermediate anion at the same temperature with compounds of formula III as exemplified in *J. Med. Chem.* (2003), 46, 3865 (see Scheme 2).

Scheme 2

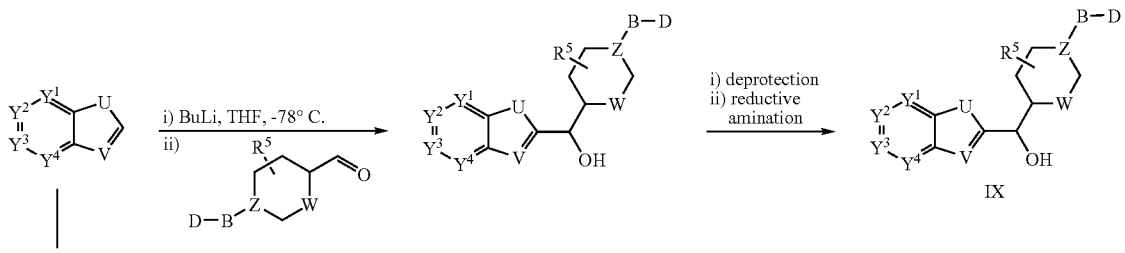

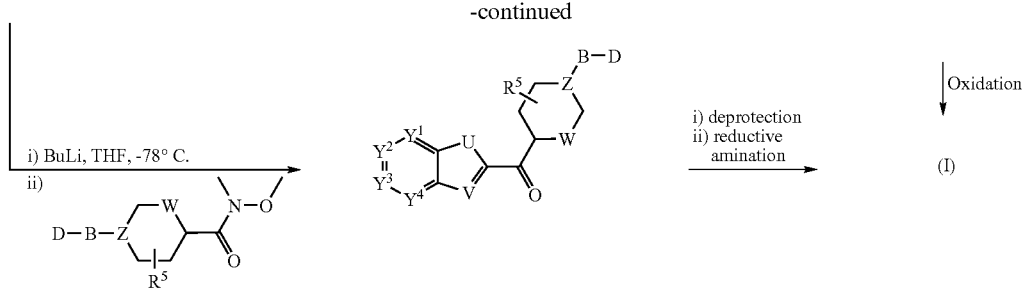

In case Z—B is CH—NH—CH$_2$— (i.e. R$^8$ is H), the nitrogen is transiently protected (see Scheme 2) by benzyloxycarbonyl, tert-butoxy or allyloxycarbonyl.

The reactions to obtain compounds of formula I wherein A is O or S are preferably carried out by treating compounds of formula VII between −100 and +20° C., and preferably between −78 and −20° C., with a strong inorganic base such as an alkali metal (e.g. sodium or potassium), an alkali metal hydride (e.g. sodium hydride), a metal alkyl (e.g. butyl lithium) or LDA, and subsequently reacting the intermediate alcoholate or thiolate with compounds of formula VI wherein X is iodine (as described in *J. Het. Chem.* (1978), 15, 337-42) in a solvent such as tetrahydrofuran (THF) between −10 and +80° C. The reaction can also be carried out in presence of CuI as described in *J. Am. Chem. Soc.* (1997), 119, 6066-6071.

Oxidation of compounds of formula VIII into compounds of formula I is performed by oxidation with MnO$_2$ or under other known methods such as Dess-Martin or Swern reactions as described in *Comprehensive Organic Transformations*, R. C. Larock Ed., Wiley-VCH New York, Chichester, Weinheim, Brisbane, Toronto (1999), pp. 1234-1249. In case Z—B is CH—NH—CH$_2$ (i.e. R$^8$ is H), the reaction is best performed after transient protection of the nitrogen function with a protecting group such as benzyloxycarbonyl, tert-butyloxycarbonyl or allyloxycarbonyl as described in Protecting groups, Kocienski, P. J., *Thieme* (1994). The protecting groups are removed after the oxidation steps using methods described in the above-mentioned reference.

The reaction between compounds of formulae IV and V is preferably carried out under the following conditions:
When Z$^1$=CH—N(R$^8$)H and L$^3$=CHO:

Reductive amination in a solvent such as THF, dichloromethane at a temperature between −10 and +80° C. in presence of reducing agents as described in *Comprehensive Organic Transformations*, R. C. Larock Ed., Wiley-VCH New York, Chichester, Weinheim, Brisbane, Toronto (1999), pp. 835-839, such as sodium borohydride or cyanoborohydride. One obtains compounds of formula I, where Z—B represents CHN(R$^8$)CH$_2$. In this reaction R$^8$ is H or C$_1$-C$_4$ alkyl.

When Z$^1$=CH—N(R$^8$)H and L$^3$=COOH:

Peptide coupling conditions in the presence of an activating agent such as 1-(dimethylaminopropyl)-3-ethylcarbodiimide hydrochloride (EDC) or 1-hydroxybenzotriazole (HOBT) or O-(7-azabenzotriazol-1-yl)-N,N,N',N'-tetramethyluronium hexafluorophosphate (HATU) as described by G. Benz in *Comprehensive Organic Synthesis*, B. M. Trost, I. Fleming, Eds; Pergamon Press: New York 1991, vol. 6, p. 381) between −20° C. and +60° C. in a dry aprotic solvent like dichloromethane, acetonitrile or dimethylformamide (DMF). One obtains a compound of formula I, where Z—B represents CH—N(R$^8$)CO.

When Z$^1$=NH and L$^3$=oxiranyl:

Epoxide opening in a dry aprotic solvent like DMF, DMSO, DMA in the presence of lithium perchlorate (1 eq) and potassium carbonate (1 eq) at temperatures between 0° C. and 120° C., preferably between 40° C. and 80° C. One obtains a compound of formula I, where Z—B represents N—CH$_2$—CH(OH).

When Z$^1$=NH and L$^3$=CH$_2$CH$_2$X, COCH$_2$X or CH$_2$COOH:

Substitution reaction in a dry aprotic solvent like dichloromethane, THF, acetonitrile or DMF in the presence of an organic base such as triethylamine or an inorganic base such as sodium carbonate between −10 and +80° C. One obtains a compound of formula I, where Z—B represents N—CH$_2$CO or N—CH$_2$CH$_2$.

The following examples illustrate the preparation of pharmacologically active compounds of the invention but do not at all limit the scope thereof.

EXAMPLES

In the following examples all temperatures are stated in ° C. All analytical and preparative HPLC investigations on non-chiral phases are performed using RP-C18 based columns. Analytical HPLC investigations are performed on two different instruments with cycle-times of ~2.5 min and ~3.5 min respectively.

ABBREVIATIONS

| | |
|---|---|
| AcOH | acetic acid |
| aq. | aqueous |
| atm | atmosphere |
| BOC | tert-butyloxycarbonyl |
| d | days |
| DCE | 1,2-dichloroethane |
| DCM | dichloromethane |
| DIPEA | N,N-diisopropylethylamine |
| DMF | N,N-dimethylformamide |
| DMSO | dimethylsulfoxide |
| EtOAc | ethyl acetate |
| ESI | Electron Spray Ionisation |
| Ether | diethyl ether |
| h | hour |
| Hex | hexane |
| LDA | lithium diisopropylamide |
| MeOH | methanol |
| min | minutes |
| MS | Mass Spectroscopy |
| quant. | quantitative |
| RT | room temperature |
| TEA | triethyl amine |
| TFA | trifluoroacetic acid |
| TLC | thin layer chromatography |
| THF | tetrahydrofuran |

Example 1

6-{[4-(benzothiazole-2-carbonyl)-cyclohexylamino]-methyl}-4H-benzo[1,4]thiazin-3-one

1.a) [trans-4-(benzothiazole-2-carbonyl)-cyclohexyl]-carbamic acid tert-butyl ester To a solution of benzothiazole (675 mg, 0.55 ml, 5 mmol) in THF (20 ml) at −78° C. was added dropwise n-BuLi (2.5M in Hex, 2 ml) such that the temperature did not exceed −70° C. The brown solution was stirred at this temperature for 15 min before dropwise addition of a solution of [trans-4-(methoxy-methyl-carbamoyl)-cyclohexyl]-carbamic acid tert-butyl ester (716 mg, 2.5 mmol, prepared according to WO 03/053933) in THF (2 ml). The temperature was kept below −70° C. The brown solution was then gradually allowed to reach RT (over 3 h). Mixture was poured into water and extracted with EtOAc. The combined organic extracts were washed with brine and dried over $MgSO_4$ and concentrated under reduced pressure. The residue was purified by chromatography over $SiO_2$ (Hex/EtOAc 4:1 then DCM). The relevant fractions were pooled, evaporated under reduced pressure, digested with Hex and filtered to give 740 mg (82%) of [4-(benzothiazole-2-carbonyl)-cyclohexyl]-carbamic acid tert-butyl ester.

$^1$H NMR (DMSO d6) δ: 8.15-8.08 (m, 1H); 7.93-7.88 (m, 1H); 7.53-7.43 (m, 2H); 4.4 (br, 1H); 3.62 (tt, J=12 Hz, J=3.2 Hz, 1H), 3.42 (br, 1H); 2.15-2.0 (m, 4H); 1.6-1.5 (m, 2H); 1.39 (s, 9H); 1.32-1.18 (m, 2H).

1.b) (trans-4-amino-cyclohexyl)-benzothiazol-2-yl-methanone

A solution of intermediate 1.a (740 mg, 2 mmol) in DCM (20 ml) was treated with TFA (2 ml). The mixture was stirred at room temperature for 2 h, concentrated in vacuo and partitioned between DCM and $NH_4OH$. The organic layer was separated, dried over $MgSO_4$ and concentrated under reduced pressure to afford the free amine (520 mg, 90%) as a yellowish foam.

MS (ESI, m/z): 261.3 [M+H$^+$].

1.c) 6-{[4-(benzothiazole-2-carbonyl)-cyclohexylamino]-methyl}-4H-benzo[1,4]thiazin-3-one A solution of intermediate 1.b (0.3 mmol) and 3-oxo-3,4-dihydro-2H-benzo[1,4]thiazine-6-carbaldehyde (0.3 mmol) in MeOH (4 ml) and dichloroethane (4 ml) was stirred at rt for 2 h. $NaBH(OAc)_3$ (0.5 mmol) was added and stirring was continued overnight. $NaBH(OAc)_3$ (0.5 mmol) was added and after 2 more hours, the solvents were removed under reduced pressure and the residue was purified by chromatography on $SiO_2$ (EtOAc, EtOAc/MeOH 9:1, EtOAc/MeOH 9:1 +1% $NH_4OH$, MeOH) to give the title compound (64 mg, 49%).

MS (ESI, m/z): 438.4 [M+H$^+$].
$^1$H NMR (DMSO d6) δ: 10.58 (s, 1H); 8.30-8.20 (m, 2H); 7.70-7.60 (m, 2H); 7.31-7.27 (m, 1H); 7.1 (br, 2H); 3.81 (br, 2H); 3.7-3.6 (m, 1H); 3.45 (s, 2H); 2.2-2.0 (m, 4H); 1.6-1.2 (m, 4H).

Example 2

6-{[trans-4-(benzothiazole-2-carbonyl)-cyclohexylamino]-methyl}-4H-benzo[1,4]oxazin-3-one The title compound was prepared according to the same protocol as for example 1, step 1.c, using however (4-amino-cyclohexyl)-benzothiazol-2-yl-methanone (0.3 mmol) and 3-oxo-3,4-dihydro-2H-benzo[1,4]oxazine-6-carbaldehyde (0.3 mmol). 40 mg (28%) of the title compound (a yellowish solid) were obtained.

MS (ESI, m/z): 422.5 [M+H$^+$].

Example 3 benzothiazol-2-yl-{trans-4-[(2,3-dihydro-benzo[1,4]dioxin-6-ylmethyl)-amino]-cyclohexyl}-methanone The title compound was prepared according to the same protocol as for example 1, step 1.c, using however (trans-4-amino-cyclohexyl)-benzothiazol-2-yl-methanone (0.3 mmol) and 2,3-dihydro-benzo[1,4]dioxine-6-carbaldehyde (0.3 mmol). 93 mg (68%) of a beige solid were obtained.

MS (ESI, m/z): 409.1 [M+H$^+$]

Example 4

6-{[trans-4-(4-methyl-benzothiazole-2-carbonyl)-cyclohexylamino]-methyl}-4H-benzo[1,4]thiazin-3-one Using 4-methyl-benzothiazole (5 mmol, obtained by reductive deamination of 2-amino-4-methylbenzothiazole), [trans-4-(methoxy-methyl-carbamoyl)-cyclohexyl]-carbamic acid tert-butyl ester (2.5 mmol) and 3-oxo-3,4-dihydro-2H-benzo[1,4]thiazine-6-carbaldehyde (0.3 mmol) in according to the same protocol as that described for example 1, steps 1.a to 1.c, the title compound was obtained as a yellowish solid (55 mg).

MS (ESI, m/z): 452.1 [M+H$^+$]
$^1$H NMR (CDCl$_3$) δ: 10.53 (s, 1H); 8.06-8.03 (m, 1H); 7.56-7.44 (m, 2H); 7.27-7.24 (m, 1H); 7.0-6.95 (m, 2H); 3.73 (br, 2H); 3.7-3.6 (m, 1H); 3.44 (s, 2H); 2.76 (s, 3H); 2.2-2.0 (m, 4H); 1.6-1.1 (m, 4H).

Example 5

{trans-4-[(2,3-dihydro-benzo[1,4]dioxin-6-ylmethyl)-amino]-cyclohexyl}-(4-methyl-benzothiazol-2-yl)-methanone Using 4-methyl-benzothiazole (5 mmol), [trans-4-(methoxy-methyl-carbamoyl)-cyclohexyl]-carbamic acid tert-butyl ester (2.5 mmol) and 2,3-dihydro-benzo[1,4]dioxine-6-carbaldehyde (0.3 mmol) according to the same protocol as that described for example 1, steps 1.a to 1.c, the title compound was obtained as a colourless solid (58 mg).

MS (ESI, m/z): 423.6 [M+H$^+$].

Example 6

{trans-4-[(2,3-dihydro-benzo[1,4]dioxin-6-ylmethyl)-amino]-cyclohexyl}-(5-methoxy-benzothiazol-2-yl)-methanone Using 5-methoxy-benzothiazole (5 mmol; *Tetrahedron* (1997), 53, 17029), [trans-4-(methoxy-methyl-carbamoyl)-cyclohexyl]-carbamic acid tert-butyl ester (2.5 mmol) and 2,3-dihydro-benzo[1,4]dioxine-6-carbaldehyde (0.3 mmol) according to the same protocol as that described for example 1, steps 1.a to 1.c, the title compound was obtained as a yellowish solid (92 mg).

MS (ESI, m/z): 439.5 [M+H$^+$].

Example 7

6-{[trans-4-(6-methoxy-benzothiazole-2-carbonyl)-cyclohexylamino]-methyl}-4H-benzo[1,4]thiazin-3-one Using 6-methoxy-benzothiazole (5 mmol; obtained by reductive deamination of 2-amino-6-methoxybenzothiazole, *J. Org. Chem.* (1980), 45, 2243), trans-[trans-4-(methoxy-methyl-carbamoyl)-cyclohexyl]-carbamic acid tert-butyl ester (2.5 mmol) and 3-oxo-3,4-dihydro-2H-benzo[1,4]thiazine-6-carbaldehyde (0.3 mmol) according to the same protocol as that described for example 1, steps 1.a to 1.c, the title compound was obtained as a yellowish solid (64 mg).

MS (ESI, m/z): 468.3 [M+H$^+$].

Example 8

6-{[trans-4-(6-methoxy-benzothiazole-2-carbonyl)-cyclohexylamino]-methyl}-4H-benzo[1,4]oxazin-3-one The title compound was prepared according to the same protocol as that described for example 1, steps 1.a to 1.c, using 6-methoxy-benzothiazole (5 mmol), [trans-4-(methoxy-methyl-carbamoyl)-cyclohexyl]-carbamic acid tert-butyl ester (2.5 mmol) and 3-oxo-3,4-dihydro-2H-benzo[1,4]oxazine-6-carbaldehyde (0.3 mmol). A yellowish solid (43 mg) was obtained.

MS (ESI, m/z): 452.4 [M+H$^+$].

Example 9

{trans-4-[(2,3-dihydro-benzo[1,4]dioxin-6-ylmethyl)-amino]-cyclohexyl}-(6-methoxy-benzothiazol-2-yl)-methanone Using 6-methoxy-benzothiazole (5 mmol), [trans-4-(methoxy-methyl-carbamoyl)-cyclohexyl]-carbamic acid tert-butyl ester (2.5 mmol) and 2,3-dihydro-benzo[1,4]dioxine-6-carbaldehyde (0.3 mmol) according to the same protocol as that described for example 1, steps 1.a to 1.c, the title compound was obtained as a yellowish solid (92 mg).

MS (ESI, m/z): 439.5 [M+H$^+$]

Example 10

6-{[trans-4-(4-methoxy-benzothiazole-2-carbonyl)-cyclohexylamino]-methyl}-4H-benzo[1,4]thiazin-3-one Using 4-methoxy-benzothiazole (5 mmol), [trans-4-(methoxy-methyl-carbamoyl)-cyclohexyl]-carbamic acid tert-butyl ester (2.5 mmol) and 3-oxo-3,4-dihydro-2H-benzo[1,4]thiazine-6-carbaldehyde (0.3 mmol) according to the same protocol as that described for example 1, steps 1.a to 1.c, the title compound was obtained as a yellow solid (45 mg).

MS (ESI, m/z): 468.4 [M+H$^+$]

Example 11

6-{[trans-4-(4-methoxy-benzothiazole-2-carbonyl)-cyclohexylamino]-methyl}-4H-benzo[1,4]oxazin-3-one The title compound was prepared according to the same protocol as that described for example 1, steps 1.a to 1.c, using 4-methoxy-benzothiazole (5 mmol), [trans-4-(methoxy-methyl-carbamoyl)-cyclohexyl]-carbamic acid tert-butyl ester (2.5 mmol) and 3-oxo-3,4-dihydro-2H-benzo[1,4]oxazine-6-carbaldehyde (0.3 mmol). An orange solid (74 mg) was obtained.

MS (ESI, m/z): 452.4 [M+H$^+$].

Example 12

{trans-4-[(2,3-dihydro-benzo[1,4]dioxin-6-ylmethyl)-amino]-cyclohexyl}-(4-methoxy-benzothiazol-2-yl)-methanone Using 4-methoxy-benzothiazole (5 mmol), [trans-4-(methoxy-methyl-carbamoyl)-cyclohexyl]-carbamic acid tert-butyl ester (2.5 mmol) and 2,3-dihydro-benzo[1,4]dioxine-6-carbaldehyde (0.3 mmol) according to the same protocol as that described for example 1, steps 1.a to 1.c, the title compound was obtained as a off-white solid (41 mg).

MS (ESI, m/z): 439.6 [M+H$^+$].

Example 13

{trans-4-[(benzothiazol-2-ylmethyl)-amino]-cyclohexyl}-(4-methoxy-benzothiazol-2-yl)-methanone Using 4-methoxy-benzothiazole (5 mmol), [trans-4-(methoxy-methyl-carbamoyl)-cyclohexyl]-carbamic acid tert-butyl ester (2.5 mmol) and benzothiazole-2-carbaldehyde (0.3 mmol) according to the same protocol as that described for example 1, steps 1.a to 1.c, the title compound was obtained as a yellow solid (66 mg).

MS (ESI, m/z): 438.4 [M+H$^+$].

Example 14

6-{[trans-4-(4-ethoxy-benzothiazole-2-carbonyl)-cyclohexylamino]-methyl}-4H-benzo[1,4]thiazin-3-one Using 4-ethoxy-benzothiazole (5 mmol), [trans-4-(methoxy-methyl-carbamoyl)-cyclohexyl]-carbamic acid tert-butyl ester (2.5 mmol) and 3-oxo-3,4-dihydro-2H-benzo[1,4]thiazine-6-carbaldehyde (0.3 mmol) according to the same protocol as that described for example 1, steps 1.a to 1.c, the title compound was obtained as a yellow solid (15 mg).

MS (ESI, m/z): 482.2 [M+H$^+$].

Example 15

6-{[trans-4-(4-ethoxy-benzothiazole-2-carbonyl)-cyclohexylamino]-methyl}-4H-benzo[1,4]oxazin-3-one The title compound was prepared according to the same protocol as that described for example 1, steps 1.a to 1.c, starting from 4-ethoxy-benzothiazole (5 mmol), [trans-4-(methoxy-methyl-carbamoyl)-cyclohexyl]-carbamic acid tert-butyl ester (2.5 mmol) and 3-oxo-3,4-dihydro-2H-benzo[1,4]oxazine-6-carbaldehyde (0.3 mmol). A yellowish solid (9 mg) was obtained.

MS (ESI, m/z): 466.1 [M+H$^+$].

Example 16

{trans-4-[(2,3-dihydro-benzo[1,4]dioxin-6-ylmethyl)-amino]-cyclohexyl}-(4-ethoxy-benzothiazol-2-yl)-methanone Using 4-ethoxy-benzothiazole (5 mmol), [trans-4-(methoxy-methyl-carbamoyl)-cyclohexyl]-carbamic acid tert-butyl ester (2.5 mmol) and 2,3-dihydro-benzo[1,4]dioxine-6-carbaldehyde (0.3 mmol) according to the same protocol as that described for example 1, steps 1.a to 1.c, the title compound was obtained as an off-white solid (6 mg).
MS (ESI, m/z): 435.1 [M+H$^+$].

Example 17

6-{[trans-4-(4-methoxy-7-methyl-benzothiazole-2-carbonyl)-cyclohexylamino]-methyl}-4H-benzo[1,4]thiazin-3-one Using 4-methoxy-7-methyl-benzothiazole (5 mmol; *J. Org. Chem.* (1984), 49, 997), [trans-4-(methoxy-methyl-carbamoyl)-cyclohexyl]-carbamic acid tert-butyl ester (2.5 mmol) and 3-oxo-3,4-dihydro-2H-benzo[1,4]thiazine-6-carbaldehyde (0.3 mmol) according to the same protocol as that described for example 1, steps 1.a to 1.c, the title compound was obtained as a yellowish solid (20 mg).
MS (ESI, m/z): 482.3 [M+H$^+$].

Example 18

{trans-4-[(2,3-dihydro-benzo[1,4]dioxin-6-ylmethyl)-amino]-cyclohexyl}-(4-methoxy-7-methyl-benzothiazol-2-yl)-methanone Using 4-methoxy-7-methyl-benzothiazole (5 mmol), [trans-4-(methoxy-methyl-carbamoyl)-cyclohexyl]-carbamic acid tert-butyl ester (2.5 mmol) and 2,3-dihydro-benzo[1,4]dioxine-6-carbaldehyde (0.3 mmol) according to the same protocol as that described for example 1, steps 1.a to 1.c, the title compound was obtained as a yellowish solid (20 mg).
MS (ESI, m/z): 453.1 [M+H$^+$].

Example 19

6-{[trans-4-(benzo[b]thiophene-2-carbonyl)-cyclohexylamino]-methyl}-4H-benzo[1,4]thiazin-3-one Using thianaphthene (5 mmol), [trans-4-(methoxy-methyl-carbamoyl)-cyclohexyl]-carbamic acid tert-butyl ester (2.5 mmol) and 3-oxo-3,4-dihydro-2H-benzo[1,4]thiazine-6-carbaldehyde (0.4 mmol) according to the same protocol as that described for example 1, steps 1.a to 1.c, the title compound was obtained as a yellowish solid (35 mg).
MS (ESI, m/z): 437.1 [M+H$^+$].

Example 20

6-{[trans-4-(benzo[b]thiophene-2-carbonyl)-cyclohexylamino]-methyl}-4H-benzo[1,4]oxazin-3-one The title compound was prepared according to the same protocol as that described for example 1, steps 1.a to 1.c, starting from thianaphthene (5 mmol), [trans-4-(methoxy-methyl-carbamoyl)-cyclohexyl]-carbamic acid tert-butyl ester (2.5 mmol) and 3-oxo-3,4-dihydro-2H-benzo[1,4]oxazine-6-carbaldehyde (0.4 mmol). A colourless solid (44 mg) was obtained.
MS (ESI, m/z): 421.1 [M+H$^+$].

Example 21 benzo[b]thiophen-2-yl-{trans-4-[(2,3-dihydro-benzo[1,4]dioxin-6-ylmethyl)-amino]-cyclohexyl}-methanone Using thianaphthene (5 mmol), [trans-4-(methoxy-methyl-carbamoyl)-cyclohexyl]-carbamic acid tert-butyl ester (2.5 mmol) and 2,3-dihydro-benzo[1,4]dioxine-6-carbaldehyde (0.4 mmol) according to the same protocol as that described for example 1, steps 1.a to 1.c, the title compound was obtained as a colourless oil which solidified on standing (50 mg).
MS (ESI, m/z): 408.2 [M+H$^+$].

Example 22

6-{[trans-4-(thiazolo[5,4-b]pyridine-2-carbonyl)-cyclohexylamino]-methyl}-4H-benzo[1,4]thiazin-3-one Using thiazolo[5,4-b]pyridine (10 mmol; *Synthesis* (1974), 120), [trans-4-(methoxy-methyl-carbamoyl)-cyclohexyl]-carbamic acid tert-butyl ester (5 mmol) and 3-oxo-3,4-dihydro-2H-benzo[1,4]thiazine-6-carbaldehyde (0.38 mmol) according to the same protocol as that described for example 1, steps 1.a to 1.c, the title compound was obtained as its hydrochloride salt (20 mg).
MS (ESI, m/z): 439.6 [M+H$^+$].

Example 23

6-{[trans-4-(4-methoxy-benzothiazole-2-carbonyl)-cyclohexylamino]-methyl}-4H-pyrido[3,2-b][1,4]thiazin-3-one 23.a) {trans-4-[hydroxy-(4-methoxy-benzothiazol-2-yl)-methyl]-cyclohexyl}-carbamic acid tert-butyl ester To a solution of 4-methoxy-benzothiazole (1.65 g, 10 mmol) in THF (50 ml) was added dropwise n-BuLi (2.5M in hexanes, 4 ml) so that the temperature did not exceed −70° C. The brown solution was stirred at this temperature for 15 min before dropwise addition of a solution of (4-formyl-cyclohexyl)-carbamic acid tert-butyl ester (1.14 g, 5 mmol) in THF (10 ml). The temperature was kept below −70° C. The brown solution was then gradually allowed to reach RT (over 3 h). The reaction mixture was quenched with saturated NH$_4$Cl solution and extracted with EtOAc. The organic layer was washed with brine and dried over MgSO$_4$ and concentrated under reduced pressure. The product was crystallised from ether to give 1.04 g (53%) of a white solid.
MS (ESI, m/z): 393.4 [M+H$^+$].

23.b) (trans-4-amino-cyclohexyl)-(4-methoxy-benzothiazol-2-yl)-methanol

A solution of intermediate 23.a (1.04 g, 2.67 mmol) in DCM (40 ml) was treated with TFA (6 ml). The mixture was stirred at RT for 2 h, concentrated in vacuo and partitioned between DCM and NH$_4$OH. The organic layer was dried over MgSO4 and concentrated under reduced pressure, affording 650 mg (83%) of a colourless solid.
MS (ESI, m/z): 293.3 [M+H$^+$].

23.c) 6-({trans-4-[hydroxy-(4-methoxy-benzothiazol-2-yl)-methyl]-cyclohexylamino}-methyl)-4H-pyrido[3,2-b][1,4]thiazin-3-one A solution of intermediate 23.b (292.4 mg, 1 mmol) and 3-oxo-3,4-dihydro-2H-pyrido[3,2-b][1,4]thiazine-6-carbaldehyde (194 mg, 1 mmol) in MeOH (4 ml) and DCE (4 ml) was stirred at RT overnight. NaBH$_4$ (74 mg, 2 mmol) was added and stirring was continued for 2 hours. The mixture was partitioned between DCM and NH$_4$OH. The organic layer was dried over MgSO$_4$, concentrated under reduced pressure and crystallised from ether to give 350 mg (74%) of colourless solid.
MS (ESI, m/z): 471.5 [M+H$^+$].

23.d) {trans-4-[hydroxy-(4-methoxy-benzothiazol-2-yl)-methyl]-cyclohexyl}-(3-oxo-3,4-dihydro-2H-pyrido[3,2-b][1,4]thiazin-6-ylmethyl)-carbamic acid tert-butyl ester To a solution of intermediate 23.c (350 mg, 0.744 mmol) in THF (50 ml) was added (BOC)$_2$O (2 eq). The mixture was stirred at RT until completion of the reaction as monitored by TLC. The volatiles were removed under reduced pressure and the residue was purified by chromatography on SiO$_2$ (EtOAc) to give 432 mg (quant.) of yellowish oil.

23.e) [trans-4-(4-methoxy-benzothiazole-2-carbonyl)-cyclohexyl]-(3-oxo-3,4-dihydro-2H-pyrido[3,2-b][1,4]thiazin-6-ylmethyl)-carbamic acid tert-butyl ester To a solution of intermediate 23.d (432 mg, 0.757 mmol) in DCM (10 ml) was added a solution of Dess Martin periodinane (15% w/w in DCM, 1.2 eq). The mixture was stirred at rt overnight, diluted with DCM and washed with saturated bicarbonate solution. The organic layer was dried over MgSO$_4$ and concentrated under reduced pressure. The residue was purified by chromatography on SiO$_2$ (Hex/EtOAc 1:1) affording 406 mg (94%) of yellowish solid.
MS (ESI, m/z): 569.4 [M+H$^+$].

23.f) 6-{[trans-4-(4-methoxy-benzothiazole-2-carbonyl)-cyclohexylamino]-methyl}-4H-pyrido[3,2-b][1,4]thiazin-3-one A solution of intermediate 23.e (100 mg, 0.18 mmol) in DCM (4 ml) was treated with TFA (1 ml). The mixture was stirred at RT for 4 h, concentrated in vacuo and partitioned between DCM and NH$_4$OH. The organic layer was dried over MgSO$_4$ and concentrated under reduced pressure. Crystallisation from MeOH/ether gave 40 mg (49%) of a yellowish solid.
MS (ESI, m/z): 469.1 [M+H$^+$].

Example 24

6-({trans-4-[(4-methoxy-benzothiazol-2-yl)-methoxyimino-methyl]-cyclohexylamino}-methyl)-4H-pyrido[3,2-b][1,4]thiazin-3-one 24.a) {trans-4-[(4-methoxy-benzothiazol-2-yl)-methoxyimino-methyl]-cyclohexyl}-(3-oxo-3,4-dihydro-2H-pyrido[3,2-b][1,4]thiazin-6-ylmethyl)-carbamic acid tert-butyl ester To a solution of intermediate 23.e (100 mg, 0.18 mmol) in pyridine (2 ml) was added O-methylhydroxylamine hydrochloride (29 mg, 2 eq) and the clear solution was stirred at RT overnight. The reaction mixture was concentrated in vacuo and the residue partitioned between EtOAc and 0.1M HCl. The organic layer was dried over MgSO$_4$ and concentrated to give 105 mg (99%) of a colourless solid.
MS (ESI, m/z): 598.4 [M+H$^+$].

24.b) 6-({trans-4-[(4-methoxy-benzothiazol-2-yl)-methoxyimino-methyl]-cyclohexylamino}-methyl)-4H-pyrido[3,2-b][1,4]thiazin-3-one A solution of intermediate 24.a (100 mg, 0.17 mmol) in DCM (4 ml) was treated with TFA (2 ml). The mixture was stirred at RT for 4 h, concentrated in vacuo and partitioned between DCM and NH$_4$OH. The organic layer was dried over MgSO$_4$ and concentrated. Crystallisation from MeOH/ether gave 40 mg (48%) as a mixture of syn and anti oximes (7:1) as colourless solid.
MS (ESI, m/z): 498.2 [M+H$^+$].
Major Isomer:
$^1$H NMR (DMSO d6) δ: 10.88 (s, 1H); 7.76-7.66 (m, 2H); 7.59-7.55 (m, 1H); 7.14-7.06 (m, 2H); 4.07 (s, 3H); 3.99 (s, 23H); 3.77 (s, 2H); 3.53 (s, 2H); 3.5-3.3 (m, 1H); 2.5-2.4 (m, 1H); 2.0-1.9 (m, 4H); 1.5-1.4 (m, 2H); 1.3-1.0 (m, 2H).

Example 25

6-{[trans-4-(4-methoxy-benzoxazole-2-carbonyl)-cyclohexylamino]-methyl}-4H-benzo[1,4]oxazin-3-one 25.a) [trans-4-(benzoxazol-2-yl-hydroxy-methyl)-cyclohexyl]-carbamic acid tert-butyl ester To a solution of 4-methoxy-benzoxazole (1490 mg, 10 mmol, obtained by methylation of 4-hydroxybenzoxazole (*J. Med. Chem.* (1987), 30, 62) in THF (60 ml) was added dropwise a solution of i-PrMgCl (5 ml, 2M solution in THF). The red mixture was stirred at 0° C. for 1 h before dropwise addition of (4-formyl-cyclohexyl)-carbamic acid tert-butyl ester (1360 mg, 6 mmol) dissolved in THF (10 ml). The reaction was stirred at 0° C. for 30 min and at RT for 1 h. The reaction mixture was quenched with aq. ammonium chloride solution and extracted EtOAc. The combined organic layers were dried over MgSO$_4$ and concentrated under reduced pressure. The residue was purified by chromatography on SiO$_2$ (hex/EtOAc 2:1, 1:1) affording 1300 mg (59%) of product as yellow oil.
MS (ESI, m/z): 377.5 [M+H$^+$].

25.b) [trans-4-(4-methoxy-benzoxazole-2-carbonyl)-cyclohexyl]-carbamic acid tert-butyl ester MnO$_2$ (3 g, 34.6 mmol) was added to a solution of intermediate 25.a (1300 mg, 3.46 mmol) in DCM (30 ml). The mixture was stirred at RT for 2 h and filtered over Celite. The filter cake was washed with DCM and the filtrate was concentrated under reduced pressure and purified by chromatography on SiO$_2$ (hex/EtOAc 2:1) to give 900 mg (70%) of a beige solid.
MS (ESI, m/z): 375.6 [M+H$^+$].

25.c) trans-(4-amino-cyclohexyl)-(4-methoxy-benzooxazol-2-yl)-methanone

A solution of intermediate 25.b (890 mg, 2.4 mmol) in DCM (10 ml) was treated with TFA (4 ml). The mixture was stirred at RT for 2 h, concentrated in vacuo, partitioned between DCM and NH$_4$OH. The organic layer was dried over MgSO$_4$ and concentrated. Chromatography on SiO$_2$ (EtOAc/MeOH 9:1 +1% NH$_4$OH) gave 350 mg (52%) of a beige solid.

25.d) 6-{[trans-4-(4-methoxy-benzooxazole-2-carbonyl)-cyclohexylamino]-methyl}-4H-benzo[1,4]oxazin-3-one The title compound was prepared thanks to the same protocol as for example 1, step 1.c, using intermediate 25.c (0.6 mmol) and 3-oxo-3,4-dihydro-2H-benzo[1,4]thiazine-6-carbaldehyde (0.6 mmol). 20 mg (7%) of a beige solid were obtained.
MS (ESI, m/z): 452.2 [M+H$^+$].

Example 26

(2,3-dihydro-benzo[1,4]dioxin-6-ylmethyl)-[trans-4-(4-methoxy-benzothiazol-2-yloxy)-cyclohexyl]-amine 26.a) [trans-4-(4-methoxy-benzothiazol-2-yloxy)-cyclohexyl]-carbamic acid tert-butyl ester trans-(4-hydroxy-cyclohexyl)-carbamic acid tert-butyl ester (2.15 g, 10 mmol) and 2-chloro-4-methoxybenzothiazole (1.99 g, 10 mmol) were dissolved in THF (50 ml) and cooled to 0° C. At this temperature, NaH dispersion (960 mg, 2.2 eq) was added portionwise and the mixture was heated at 60° C. for 2 h. DMF (20 ml) was added and heating was continued for 1 h. The mixture was poured into water and extracted with EtOAc. The organic layer was washed with water and brine, dried over MgSO$_4$ and concentrated under reduced pressure. Purification by chromatograpy on SiO$_2$ (hex/EtOAc 4:1, 2:1) gave 1 g (26%) of a beige solid.
MS (ESI, m/z): 379.5 [M+H$^+$].

26.b) trans-4-(4-methoxy-benzothiazol-2-yloxy)-cyclohexylamine

Intermediate 26.a (1 g, 2.64 mmol) was dissolved in DCM (25 ml) and TFA (4 ml) was added. The mixture was stirred at RT for 3 h, concentrated in vacuo and partitioned between DCM and NH$_4$OH. The organic layer was dried over MgSO$_4$ and concentrated, affording 570 mg (79%) of red solid.
MS (ESI, m/z): 279.5 [M+H$^+$].

26.c) (2,3-dihydro-benzo[1,4]dioxin-6-ylmethyl)-[trans-4-(4-methoxy-benzothiazol-2-yloxy)-cyclohexyl]-amine Intermediate 26.b (0.5 mmol) and 3-oxo-3,4-dihydro-2H-benzo[1,4]oxazine-6-carbaldehyde (0.3 mmol) were dissolved in DCE (4 ml) and MeOH (4 ml). The mixture was stirred at RT overnight, NaBH$_4$ (1 eq) was added and stirring continued for 1 h. Mixture was partitioned between DCM and NH$_4$OH. The organic layer was dried over MgSO$_4$ and concentrated under reduced pressure. Purification by chromatography (EtOAc/MeOH 9:1 +1% NH$_4$OH) gave 155 mg (73%) of the title compound as an off-white solid.
MS (ESI, m/z): 427.2 [M+H$^+$].

Example 27

6-{[trans-4-(4-methoxy-benzothiazol-2-yloxy)-cyclohexylamino]-methyl}-4H-benzo[1,4]oxazin-3-one trans-4-(4-methoxy-benzothiazol-2-yloxy)-cyclohexylamine (0.5 mmol, intermediate 25.b) and 3-oxo-3,4-dihydro-2H-benzo[1,4]oxazine-6-carbaldehyde (0.5 mmol) were dissolved in DCE (4 ml) and MeOH (4 ml). The mixture was stirred at RT overnight, NaBH$_4$ (1 eq) was added and stirring continued for 1 h. The reaction mixture was partitioned between DCM and NH$_4$OH. The organic layer was dried over MgSO$_4$ and concentrated under reduced pressure. Purification by chromatography (EtOAc/MeOH 9:1 +1% NH$_4$OH) and crystallisation from ether gave 36 mg (16%) of the title compound as a colourless solid.
MS (ESI, m/z): 440.6 [M+H$^+$].

Example 28

6-{[trans-4-(4-methoxy-benzothiazol-2-yloxy)-cyclohexylamino]-methyl}-4H-benzo[1,4]thiazin-3-one This compound was prepared using the same method as that of Example 27, 0.3 mmol of 3-oxo-3,4-dihydro-2H-benzo[1,4]thiazine-6-carbaldehyde replacing however the 0.5 mmol of 3-oxo-3,4-dihydro-2H-benzo[1,4]oxazine-6-carbaldehyde. Purification by chromatography (EtOAc/MeOH 9:1 +1% NH$_4$OH) gave 134 mg (59%) of the title compound as a yellowish foam.
MS (ESI, m/z): 456.4 [M+H$^+$].
$^1$H NMR (DMSO d6) δ: 10.62 (s, 1H); 7.43 (d, J=7.95, 1H); 7.35-7.21 (m, 2H); 7.1-7.0 (m, 3H); 3.93 (s, 3H); 3.80 (br, 2H); 3.47 (br, 2H); 2.75-2.6 (m, 1H); 2.3-2.0 (m, 4H); 16-1.3 (m, 5H).

Example 29

(3R,6S)-6-{[6-(4-methoxy-benzothiazole-2-carbonyl)-tetrahydro-pyran-3-ylamino]-methyl}-4H-pyrido[3,2-b][1,4]thiazin-3-one 29.a) (3R,6S)-(6-formyl-tetrahydro-pyran-3-yl)-carbamic acid tert-butyl ester To a solution of oxalyl chloride (3.5 ml) in DCM (25 ml) cooled to −78° C., was added drop wise a solution of DMSO (3.5 ml) in DCM (25 ml). After 15 minutes stirring, a solution of (3R,6S)-(6-hydroxymethyl-tetrahydro-pyran-3-yl)-carbamic acid tert-butyl ester (prepared as described in *Eur. J. Org. Chem.* (2003), 2418-2427; 3 g) in DCM (25 ml) was added drop wise. The reaction was stirred 1 h and a solution of triethylamine (15 ml) in DCM (15 ml) was added dropwise. The reaction proceeded for 1 hour, with warming to 0° C. Saturated sodium bicarbonate (50 ml) was added. The organic layer was separated, dried over sodium sulfate, filtered and concentrated in vacuo. The residue was chromatographed (Hex/EtOAc 1:2) to afford the title aldehyde (2.5 g) as a colorless solid.

29.b) (3R,6S)-6-{[6-(4-methoxy-benzothiazole-2-carbonyl)-tetrahydro-pyran-3-ylamino]-methyl}-4H-pyrido[3,2-b][1,4]thiazin-3-one Using the same method as for Example 23, steps 23.a to 23.f, the title compound was synthesised from 4-methoxy-benzothiazole, (3R,6S)-(6-formyl-tetrahydro-pyran-3-yl)-carbamic acid tert-butyl ester and 3-oxo-3,4-dihydro-2H-pyrido[3,2-b][1,4]thiazine-6-carbaldehyde. After chromatography on SiO$_2$ (EtOAc/MeOH 9:1 +1% NH$_4$OH) and crystallisation from ether/MeOH, a yellowish solid (30 mg) was obtained.
$^1$H NMR (DMSO d6) δ: 10.91 (s, 1H); 7.8-7.7 (m, 2H); 7.60 (t, J=8.1, 1H); 7.17 (d, J=8.1, 1H); 7.12 (d, J=8.1, 1H); 5.10-5.05 (m, 1H); 4.15-4.05 (m, 1H); 4.02 (s, 3H); 3.83 (s, 2H); 3.61 (s, 2H); 3.21 (t, J=10.6, 1H); 3.7-3.5 (m, 1H); 2.28-2.10 (m, 2H); 1.6-1.4 (m, 2H)

MS (ESI, m/z): 471.4 [M+H$^+$].

Example 30

(3R,6S)-6-{[6-(4-methoxy-benzothiazole-2-carbonyl)-tetrahydro-pyran-3-ylamino]-methyl}-4H-benzo[1,4]thiazin-3-one Using the same protocol as for example 23, steps 23.a) to 23.f, the title compound was synthesised using 4-methoxy-benzothiazole (8.7 mmol), (3R,6S)-(6-formyl-tetrahydro-pyran-3-yl)-carbamic acid tert-butyl ester (4.6 mmol) and 3-oxo-3,4-dihydro-2H-benzo[1,4]thiazine-6-carbaldehyde (0.7 mmol) and obtained after chromatography on SiO$_2$ (EtOAc/MeOH 9:1 +1% NH$_4$OH) and crystallisation from ether/MeOH as a yellowish solid (35 mg).

MS (ESI, m/z): 470.2 [M+H$^+$].

Example 31

(3R,6S)-6-({6-[hydroxyimino-(4-methoxy-benzothiazol-2-yl)-methyl]-tetrahydro-pyran-3-ylamino}-methyl)-4H-pyrido[3,2-b][1,4]thiazin-3-one A solution of (3R,6S)-6-{[6-(4-methoxy-benzothiazole-2-carbonyl)-tetrahydro-pyran-3-ylamino]-methyl}-4H-pyrido[3,2-b][1,4]thiazin-3-one (Example 29, 47 mg, 0.1 mmol), and hydroxylamine hydrochloride (5 eq) in pyridine (1 ml) was stirred at RT overnight. The mixture was concentrated in vacuo and partitioned between NH$_4$OH and DCM. The organic layers were dried over MgSO$_4$ and concentrated. Chromatography on SiO$_2$ (EtOAc/MeOH 9:1 +1% NH$_4$OH) gave the title compound as yellow solid (10 mg, 20%).

MS (ESI, m/z): 486.3 [M+H$^+$].

Example 32

{1-[2-(2,3-dihydro-benzo[1,4]dioxin-6-yl)-ethyl]-piperidin-4-yl}-(4-methoxy-benzothiazol-2-yl)-methanone 32.a) 4-(4-methoxy-benzothiazole-2-carbonyl)-piperidine-1-carboxylic acid tert-butyl ester To a solution of 4-methoxybenzothiazole (413 mg, 2.5 mmol) in THF (10 ml) at −75° C. was added dropwise n-BuLi (2.5M in Hex, 1.1 ml) such that the temperature did not exceed −70° C. The brown solution was stirred at this temperature for 15 min before the dropwise addition of a solution of 4-(methoxy-methyl-carbamoyl)-piperidine-1-carboxylic acid tert-butyl ester (680 mg, 2.5 mmol) in THF (2 ml). The temperature was also kept below −70° C. The brown solution was then gradually allowed to reach RT (over 3 h). The mixture was poured on water and extracted with EtOAc. Organic extracts were washed with brine and dried over MgSO$_4$ and concentrated. Chromatography on SiO$_2$ (hex/EtOAc 2:1) gave 565 mg (60%) of a yellowish solid.

MS (ESI, m/z): 377.5 [M+H$^+$].

32.b) (4-methoxy-benzothiazol-2-yl)-piperidin-4-yl-methanone

A solution of intermediate 32.a (565 mg, 1.5 mmol) in DCM (20 ml) was treated with TFA (2 ml). The mixture was stirred at RT for 3 h, concentrated in vacuo and partitioned between DCM and NH$_4$OH. Organic layers were dried over MgSO$_4$ and concentrated to give 435 mg (100%) of a yellowish foam.

MS (ESI, m/z): 277.1 [M+H$^+$].

{1-[2-(2,3-dihydro-benzo[1,4]dioxin-6-yl)-ethyl]-piperidin-4-yl}-(4-methoxy-benzothiazol-2-yl)-methanone A mixture of intermediate 32.b (102 mg, 0.37 mmol) and toluene-4-sulfonic acid 2-(2,3-dihydro-benzo[1,4]dioxin-6-yl)-ethyl ester (115 mg, 0.344 mmol) in DMF (1 ml) was treated with DIPEA (61 µl, 0.37 mmol) and the mixture was stirred at RT overnight. The mixture was poured on water and extracted with EtOAc. The organic layers were dried over MgSO$_4$ and concentrated. Chromatography on SiO$_2$ (EtOAc, EtOAc/MeOH) gave 75 mg (46%) of title compound as a beige solid.

MS (ESI, m/z): 439.7 [M+H$^+$].

Example 33

1-(2,3-dihydro-benzo[1,4]dioxin-6-yl)-2-[4-(4-methoxy-benzothiazole-2-carbonyl)-piperidin-1-yl]-ethanone A mixture of (4-methoxy-benzothiazol-2-yl)-piperidin-4-yl-methanone (333 mg, 1.2 mmol) and 2-chloro-1-(2,3-dihydro-benzo[1,4]dioxin-6-yl)-ethanone (256 mg, 1.2 mmol) in DMF (4 ml) was treated with DIPEA (199 ul, 1.2 mmol) and the mixture was stirred at RT overnight. The mixture was poured on water and extracted with EtOAc. The organic layers were dried over MgSO$_4$ and concentrated. Chromatography on SiO$_2$ (hex/EtOAc 1:1, EtOAc) and crystallisation from ether gave 350 mg (65%) of title compound as a yellowish solid.

MS (ESI, m/z): 453.3 [M+H$^+$].

Example 34

6-{2-[4-(4-methoxy-benzothiazole-2-carbonyl)-piperidin-1-yl]-acetyl}-4H-benzo[1,4]oxazin-3-one A mixture of (4-methoxy-benzothiazol-2-yl)-piperidin-4-yl-methanone (83 mg, 0.3 mmol) and 6-(2-chloro-acetyl)-4H-benzo[1,4]oxazin-3-one (68 mg, 0.3 mmol) in DMF (1 ml) was treated with DIPEA (50 µl, 0.3 mmol) and the mixture was stirred at RT overnight. The mixture was poured on water and extracted with EtOAc. The organic layers were dried over MgSO$_4$ and concentrated. Crystallisation from ether gave 113 mg (81%) of title compound as a beige solid.

MS (ESI, m/z): 466.0 [M+H$^+$].

$^1$H NMR (CDCl$_3$) δ: 10.92 (s, 1H); 7.75 (d, J=8.1, 1H); 7.69 (dd, J=8.1, J=2.1, 1H); 7.65-7.55 (m, 2H); 7.16 (d, J=8.2, 1H); 7.05 (d, J=8.2, 1H); 4.69 (s, 2H); 4.02 (s, 3H); 3.78-3.6 (m, 3H); 3.05-2.90 (m, 2H); 2.40-2.20 (m, 2H); 2.0-1.9 (m, 2H); 1.8-1.6 (m, 2H).

Example 35

6-{2-[4-(4-methoxy-benzothiazole-2-carbonyl)-piperidin-1-yl]-acetyl}-4H-benzo[1,4]thiazin-3-one A mixture of (4-methoxy-benzothiazol-2-yl)-piperidin-4-yl-methanone (83 mg, 0.3 mmol) and 6-(2-chloro-acetyl)-4H-benzo[1,4]thiazin-3-one (72.5 mg, 0.3 mmol, prepared as described in WO 02/096907) in DMF (1 ml) was treated with DIPEA (50 µl, 0.3 mmol) and the mixture was stirred at RT overnight. The mixture was poured on water and extracted with EtOAc. The organic layers were dried over MgSO$_4$ and concentrated. Crystallisation from ether and MeOH gave 65 mg (45%) of title compound as a beige solid.

MS (ESI, m/z): 482.3 [M+H$^+$].

Example 36

{1-[2-(2,3-dihydro-benzo[1,4]dioxin-6-yl)-2-hydroxy-ethyl]-piperidin-4-yl}-(4-methoxy-benzothiazol-2-yl)-methanone 36.a) 6-oxiranyl-2,3-dihydro-benzo[1,4]dioxine To a solution of 6-methoxymethyl-2,3-dihydro-benzo[1,4]dioxine (1 g, 6.1 mmol) in acetonitrile (15 ml) was added trimethylsulfonium iodide (1.28 g, 6.27 mmol) and KOH (2.39 g, 42.6 mmol). The mixture was stirred at 60° C. for 90 min, poured on water and extracted with EtOAc. Organic extracts were washed with brine, dried over MgSO$_4$ and concentrated. Chromatography on SiO$_2$ (hex/EtOAc 2:1) gave the epoxide as a colourless oil (1 g, 92%).

$^1$H NMR (CDCl$_3$) δ: 6.8-6.6 (m, 3H); 4.17 (s, 4H); 3.70-3.66 (m, 1H); 3.05-3.00 (m, 1H); 2.70-2.66 (m, 1H).

36.b) {1-[2-(2,3-dihydro-benzo[1,4]dioxin-6-yl)-2-hydroxy-ethyl]-piperidin-4-yl}-(4-methoxy-benzothiazol-2-yl)-methanone A mixture of (4-methoxy-benzothiazol-2-yl)-piperidin-4-yl-methanone (83 mg, 0.3 mmol), 6-oxiranyl-2,3-dihydro-benzo[1,4]dioxine (53.5 mg, 0.3 mmol), lithium perchlorate (32 mg, 0.3 mmol) and potassium carbonate (42 mg, 0.3 mmol) in DMF (2 ml) was heated at 80° C. overnight. The mixture was poured on water and extracted with EtOAc. Organic extracts were washed with water and brine, dried over MgSO$_4$ and concentrated. Chromatography on SiO$_2$ (EtOAc/MeOH 9:1) gave the title compound as a beige solid (100 mg, 73%, 4:1 mixture of regioisomers).

MS (ESI, m/z): 455.6 [M+H$^+$].

BIOLOGICAL ASSAYS

In Vitro Assays
Experimental Method:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards Villanova, Pa., USA, 1997". Minimal inhibitory concentrations (MICs; mg/l) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH of the test medium was 7.2-7.3.

Results:

All Examples were tested against several Gram positive and Gram negative bacteria. Typical antibacterial spectra are given in the table hereafter (MIC in mg/l).

Compounds of formula I predominantly have MIC values of <=4 mg/l against *S. aureus* 29213, *H. influenzae* A921 and *M. catarrhalis* A894.

The invention claimed is:

1. A compound of formula I

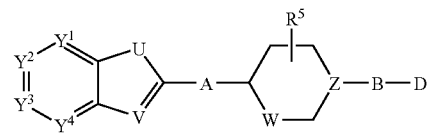

wherein:
A represents —O—, S, —C(=O)—, or —C(=NOR$^6$)—;
Z—B represents NCH$_2$CH$_2$, NCOCH$_2$, NCH$_2$CO, NCH$_2$CH(OH), CHN(R$^8$)CH$_2$ or CHN(R$^8$)CO;
D represents a group

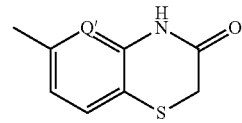

wherein Q' is —CH— or —N—;
U represents —NH—, —O— or —S—;
V represents —N— or —CH—;
W represents —CH$_2$—, —O— or —NR$^7$—;
Y$^1$ represents —CR$^1$— or —N—;
Y$^2$ represents —CR$^2$— or —N—;
Y$^3$ represents —CR$^3$— or —N—;
Y$^4$ represents —CR$^4$— or —N—;
R$^1$ represents H, methyl, ethyl or halogen;
R$^2$, R$^3$ and R$^4$ each represent independently H, C$_1$-C$_4$ alkyl, halogen, or C$_1$-C$_4$ alkoxy;
R$^5$ represents H, C$_1$-C$_4$ alkyl or fluorine;
R$^6$ represents H, C$_1$-C$_4$ alkyl or aryl-C$_1$-C$_4$ alkyl;
R$^7$ represents H, C$_1$-C$_4$ alkyl, aryl-C$_1$-C$_4$ alkyl or —CH$_2$—COOH;
R$^8$ represents H, C$_1$-C$_4$ alkyl or —CH$_2$—COOH;
with the provisos that
if Z—B represents NCH$_2$CH$_2$, NCOCH$_2$, NCH$_2$CO or NCH$_2$CH(OH), then W represents —CH$_2$—;
if A represents O or S, then W represents —CH$_2$—; and only one or two of Y$^1$, Y$^2$, Y$^3$ and Y$^4$ can represent N at the same time;
or a tautomer, an optically pure enantiomer, a mixture of enantiomers, a racemate, an optically pure diastereoisomer, a mixture of diastereoisomers, a diastereoisomeric racemate, a mixture of diastereoisomeric racemates, a meso form, or a pharmaceutically acceptable salt of the compound of formula I.

| Example No. | S. aureus 29213 | S. aureus A798 | E. faecalis 29212 | E. faecium A949 | S. pneumoniae 49619 | H influenzae A921 | M. catarrhalis A894 | E. coli 25922 | P. aeruginosa 27853 |
|---|---|---|---|---|---|---|---|---|---|
| 1 | 0.25 | 0.125 | 0.5 | 1 | 2 | 0.063 | <=0.031 | 0.5 | 16 |
| 4 | 0.125 | 0.063 | 0.5 | 0.25 | 1 | 0.25 | <=0.031 | 1 | 4 |
| 23 | 1 | 0.5 | 8 | 8 | 4 | 8 | 0.25 | 16 | >16 |
| 28 | 8 | 1 | 16 | 16 | 16 | 16 | 0.125 | 16 | >16 |
| 29 | 1 | 2 | 2 | 1 | 4 | 2 | 0.125 | 16 | >16 |
| 34 | 1 | 2 | 16 | 4 | 16 | 2 | 0.25 | 16 | >16 |

2. The compound according to claim 1, wherein A is —C(=O)—; or a pharmaceutically acceptable salt thereof.

3. The compound according to claim 1, wherein Z—B is CH—NH—CH$_2$; or a pharmaceutically acceptable salt thereof.

4. The compound according to claim 1, wherein U is —S—; or a pharmaceutically acceptable salt thereof.

5. The compound according to claim 1, wherein W is —CH$_2$—; or a pharmaceutically acceptable salt thereof.

6. The compound according to claim 1, wherein Y$^4$ is CR$^4$ and one of Y$^1$, Y$^2$ and Y$^3$ is —N— while the remaining are —CR$^1$—, —CR$^2$— or —CR$^3$— respectively; or a pharmaceutically acceptable salt thereof.

7. The compound according to claim 1, wherein Y$^1$, Y$^2$, Y$^3$ and Y$^4$ are —CR$^1$—, —CR$^2$—, —CR$^3$— and —CR$^4$— respectively; or a pharmaceutically acceptable salt thereof.

8. The compound according to claim 1, wherein R$^1$ is H; or a pharmaceutically acceptable salt thereof.

9. The compound according to claim 1, wherein R$^2$ and R$^3$ are both H; or a pharmaceutically acceptable salt thereof.

10. The compound according to claim 1, wherein R$^4$ is C$_1$-C$_3$ alkyl or C$_1$-C$_3$ alkoxy; or a pharmaceutically acceptable salt thereof.

11. The compound according to claim 1, wherein R$^5$ is H; or a pharmaceutically acceptable salt thereof.

12. The compound according to claim 1, wherein R$^8$ is H; or a pharmaceutically acceptable salt thereof.

13. The compound according to claim 1, wherein D is 4H-pyrido[3,2-b][1,4]thiazin-3-one 6-yl; or a pharmaceutically acceptable salt thereof.

14. The compound according to claim 1, wherein W is —O— and the group

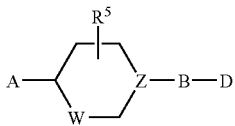

has the following partial structure:

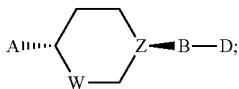

or a pharmaceutically acceptable salt of the compound.

15. The compound according to claim 1, wherein W is —CH$_2$—, R$^5$ is H, Z—B represents CHN(R$^8$)CH$_2$ or CHN(R$^8$)CO and the two substituents A and B are trans configured; or a pharmaceutically acceptable salt of the compound.

16. The compound according to claim 1 which is:
6-{[4-(benzothiazole-2-carbonyl)-cyclohexylamino]-methyl}-4H-benzo[1,4]thiazin-3-one;
6-{[trans-4-(4-methyl-benzothiazole-2-carbonyl)-cyclohexylamino]-methyl}-4H-benzo[1,4]thiazin-3-one;
6-{[trans-4-(6-methoxy-benzothiazole-2-carbonyl)-cyclohexylamino]-methyl}-4H-benzo[1,4]thiazin-3-one;
6-{[trans-4-(4-methoxy-benzothiazole-2-carbonyl)-cyclohexylamino]-methyl}-4H-benzo[1,4]thiazin-3-one;
6-{[trans-4-(4-ethoxy-benzothiazole-2-carbonyl)-cyclohexylamino]-methyl}-4H-benzo[1,4]thiazin-3-one;
6-{[trans-4-(4-methoxy-7-methyl-benzothiazole-2-carbonyl)-cyclohexylamino]-methyl}-4H-benzo[1,4]thiazin-3-one;
6-{[trans-4-(benzo[b]thiophene-2-carbonyl)-cyclohexylamino]-methyl}-4H-benzo[1,4]thiazin-3-one;
6-{[trans-4-(thiazolo[5,4-b]pyridine-2-carbonyl)-cyclohexylamino]-methyl}-4H-benzo[1,4]thiazin-3-one;
6-{[trans-4-(4-methoxy-benzothiazole-2-carbonyl)-cyclohexylamino]-methyl}-4H-pyrido[3,2-b][1,4]thiazin-3-one;
6-({trans-4-[(4-methoxy-benzothiazol-2-yl)-methoxyimino-methyl]-cyclohexylamino}-methyl)-4H-pyrido[3,2-b][1,4]thiazin-3-one;
6-{[trans-4-(4-methoxy-benzothiazol-2-yloxy)-cyclohexylamino]-methyl}-4H-benzo[1,4]thiazin-3-one;
(3R,6S)-6-{[6-(4-methoxy-benzothiazole-2-carbonyl)-tetrahydro-pyran-3-ylamino]-methyl}-4H-pyrido[3,2-b][1,4]thiazin-3-one;
(3R,6S)-6-{[6-(4-methoxy-benzothiazole-2-carbonyl)-tetrahydro-pyran-3-ylamino]-methyl}-4H-benzo[1,4]thiazin-3-one;
(3R,6S)-6-({6-[hydroxyimino-(4-methoxy-benzothiazol-2-ye-methyl]-tetrahydro-pyran-3-ylamino}-methyl)-4H-pyrido[3,2-b][1,4]thiazin-3-one;
6-{2-[4-(4-methoxy-benzothiazole-2-carbonyl)-piperidin-1-yl]-acetyl}-4H-benzo[1,4]thiazin-3-one;
or a pharmaceutically acceptable salts of the compound.

17. A pharmaceutical composition comprising, as active principle, a compound of formula I as defined in claim 1 or a pharmaceutically acceptable salt thereof, and at least one therapeutically inert excipient.

18. The compound according to claim 1, wherein D is 4H-benzo[1,4]thiazin-3-one-6-yl; or a pharmaceutically acceptable salt thereof.

* * * * *